(12) United States Patent
Menzel

(10) Patent No.: US 9,633,497 B2
(45) Date of Patent: Apr. 25, 2017

(54) SYSTEMS AND METHODS FOR MEDICAL MONITORING DEVICE GESTURE CONTROL LOCKOUT

(71) Applicant: Mindray DS USA, Inc., Mahwah, NJ (US)

(72) Inventor: Frank Menzel, Oakland, NJ (US)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 320 days.

(21) Appl. No.: 14/478,570

(22) Filed: Sep. 5, 2014

(65) Prior Publication Data

US 2016/0071341 A1    Mar. 10, 2016

(51) Int. Cl.
| | |
|---|---|
| G05B 19/00 | (2006.01) |
| G07C 9/00 | (2006.01) |
| A61B 5/00 | (2006.01) |
| H04W 12/06 | (2009.01) |
| G06F 3/01 | (2006.01) |
| G06F 19/00 | (2011.01) |
| A61B 90/90 | (2016.01) |
| A61B 90/96 | (2016.01) |
| A61B 90/98 | (2016.01) |

(52) U.S. Cl.
CPC ............ *G07C 9/00111* (2013.01); *A61B 5/00* (2013.01); *A61B 5/7475* (2013.01); *A61B 90/90* (2016.02); *A61B 90/96* (2016.02); *A61B 90/98* (2016.02); *G06F 3/017* (2013.01); *G06F 19/3406* (2013.01); *H04W 12/06* (2013.01); *A61B 5/7495* (2013.01); *A61B 2560/0487* (2013.01)

(58) Field of Classification Search
CPC ..... G07C 9/00111; A61B 90/90; A61B 90/96; A61B 90/98; G06F 3/017
See application file for complete search history.

(56) References Cited

U.S. PATENT DOCUMENTS

| | | | | |
|---|---|---|---|---|
| 8,279,091 | B1 * | 10/2012 | Tran | G06F 3/014 340/4.1 |
| 8,868,681 | B2 * | 10/2014 | Xu | A61B 5/0015 709/217 |
| 9,313,814 | B2 * | 4/2016 | Lee | H04W 76/023 |
| 9,361,530 | B2 * | 6/2016 | Sly | G06K 9/00892 |

(Continued)

*Primary Examiner* — Joseph Feild
*Assistant Examiner* — Rufus Point
(74) *Attorney, Agent, or Firm* — Kory D. Christensen; Stoel Rives LLP

(57) ABSTRACT

A medical monitoring device may include a gesture control sensor for detecting gesture commands from users. The medical monitoring device may enable gesture control when it receives an identifier from a tag and the identifier is authenticated. The tag may include an RFID tag and/or a barcode. The identifier may be authenticated locally and/or by a remote device communicatively coupled to the medical monitoring device (e.g., over a network). Once gesture control is enabled, gestures by the user may be identified by the medical monitoring device, an action corresponding to the gesture may be determined, and the action may be performed. The gesture control sensor may be disabled manually or automatically when predetermined criteria are satisfied to prevent the gesture control sensor from receiving inadvertent commands.

20 Claims, 7 Drawing Sheets

(56) References Cited

U.S. PATENT DOCUMENTS

| | | | |
|---|---|---|---|
| 2005/0025706 A1* | 2/2005 | Kagermeier | A61B 6/00 424/9.3 |
| 2005/0101314 A1* | 5/2005 | Levi | H04L 63/0861 455/423 |
| 2005/0102167 A1* | 5/2005 | Kapoor | A61B 5/0006 705/3 |
| 2009/0275805 A1* | 11/2009 | Lane | A61B 5/01 600/300 |
| 2009/0303204 A1* | 12/2009 | Nasiri | A63F 13/06 345/184 |
| 2011/0074703 A1* | 3/2011 | Black | G06F 3/0426 345/173 |
| 2012/0050043 A1* | 3/2012 | Scarola | G07C 9/00111 340/572.8 |
| 2013/0346168 A1* | 12/2013 | Zhou | G06F 1/163 705/14.4 |
| 2014/0028861 A1* | 1/2014 | Holz | H04N 5/23277 348/208.4 |
| 2014/0168062 A1* | 6/2014 | Katz | G06F 3/017 345/156 |
| 2014/0282280 A1* | 9/2014 | Pack | G06F 3/0488 715/863 |
| 2014/0298672 A1* | 10/2014 | Straker | H04W 12/06 34/175 |
| 2014/0349588 A1* | 11/2014 | Corretjer | H04M 1/72569 455/73 |
| 2015/0109193 A1* | 4/2015 | Sly | G06K 9/00892 345/156 |
| 2015/0181631 A1* | 6/2015 | Lee | H04W 76/023 455/41.2 |
| 2015/0262442 A1* | 9/2015 | Chen | G07C 9/00309 340/5.72 |
| 2015/0277703 A1* | 10/2015 | Davis | G06F 19/3406 705/2 |
| 2015/0302179 A1* | 10/2015 | Rheault | G06F 19/363 705/2 |
| 2015/0370318 A1* | 12/2015 | Yamaguchi | G06F 3/005 345/157 |

* cited by examiner

SYSTEMS AND METHODS FOR MEDICAL MONITORING DEVICE GESTURE CONTROL LOCKOUT

TECHNICAL FIELD

The present disclosure relates to medical monitoring devices and more particularly relates to systems and methods for regulating access to gesture control.

DETAILED DESCRIPTION OF PREFERRED EMBODIMENTS

Figure 1:
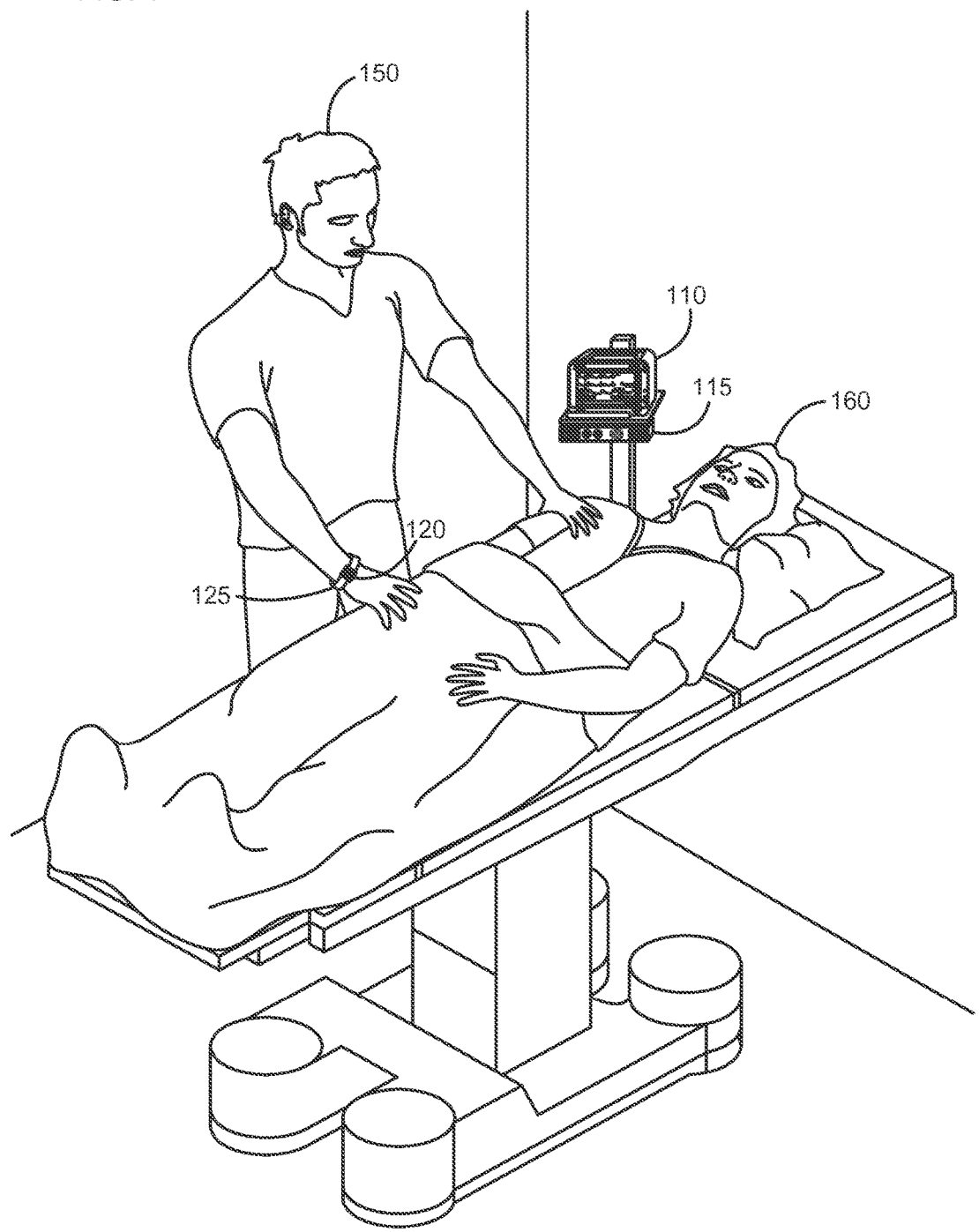
FIG. 1 is a perspective view of a medical practitioner interacting with a patient coupled to a patient monitor capable of interpreting gestures.

Modern technology practice makes extensive use of electronic monitoring of vital signs and other physiological parameters of patients. A medical monitoring device may include one or more sensors to acquire physiological data representative of the physiological condition of the patient. Medical monitoring devices may include patient monitors that display measurement data locally, telemetry devices that transmit measurement data to remote systems, and/or the like. Medical monitoring devices may include gesture control sensors that allow users to control the medical monitoring devices using gestures. For example, a medical practitioner may change the configuration and/or settings of a medical monitoring device using gestures and/or may manipulate the display of physiological data. The medical practitioner may also inadvertently control the medical monitoring device using gestures (e.g., when using gestures to communicate with the patient). Alternatively, an unauthorized user, such as the patient, may be able to intentionally or inadvertently control the medical monitoring device. As a result, the medical monitoring device may be misconfigured and may be dangerous for the patient. For example, the medical monitoring device may not signal an alarm when it should.

A medical monitoring device may disable gesture control to prevent inadvertent and/or unauthorized gestures from controlling the medical monitoring device. The medical monitoring device may disable the gesture control sensor (e.g., to reduce energy consumption) and/or may disregard gestures detected by the gesture control sensor while gesture control is disabled. A user, such as a medical practitioner, may enable the gesture control when ready to control the medical monitoring device. The medical monitoring device may then identify gestures made by the user, determine an action associated with the identified gesture, and perform the determined action. Gesture control may be automatically and/or manually disabled when the user is no longer providing gesture commands to the medical monitoring device.

The user may be able to enable gesture control by presenting a tag to the medical monitoring device. For example, the medical monitoring device may include a wireless reader, and presenting the tag may include bringing the tag within range of the wireless reader. The wireless reader may be configured to retrieve an identifier from the tag. In some embodiments, the identifier may need to be authenticated before gesture control is enabled. The medical monitoring device may determine whether gesture control is permitted for the retrieved identifier and/or which commands are permitted for the retrieved identifier. For example, the medical monitoring device may locally store indications of the rights associated with each identifier, and/or the medical monitoring device may request information about the rights from a remote device via a network (e.g., a medical center network). In an embodiment, a central database may associate identifiers with users (e.g., medical practitioners) and/or rights for various medical monitoring devices. Users may be added, be removed, and/or have their rights modified by adding, deleting, modifying, etc. corresponding entries in the central database. Alternatively, or in addition, updated information may pushed to the medical monitoring devices (e.g., each time an update is made, periodically, etc.) and/or pulled by the medical monitoring device (e.g., periodically, each time a user is authenticated, etc.).

Users may have rights to some medical monitoring devices but not others, so the medical monitoring device and/or a remote device (e.g., the central database) may determine which particular set of user rights are applicable for the medical monitoring device. For example, the medical monitoring device may identify itself to the remote device, and the remote device may report the user's right for the identified medical monitoring device. In an embodiment, the medical monitoring device may receive indications of rights for multiple monitors from the remote device and distinguish which are applicable to it. Alternatively, or in addition, the medical monitoring device may receive an indication of a class of users to which the identifier corresponds, and the medical monitoring device may distinguish which classes are permitted what types of access. Rights may be determined based on combinations of criteria, such as the user's rank in an organization hierarchy as well as a ward associated with the user, and/or the like. Once the medical monitoring device has determined what rights the user has, the medical monitoring device may indicate those rights (e.g., using a textual description of the rights, by graying out options to which the user does not have rights, etc.).

The tag may be active or passive (e.g., the tag may be powered or may not need a power source other than wireless power received from the reader). The tag may be a radio frequency identification (RFID) tag (e.g., a near field communication (NFC) tag), a barcode (e.g., a one dimensional or two dimensional barcode), text, and/or the like. Thus, the wireless reader may include a radio frequency (RF) reader, a barcode reader (e.g., a laser scanner, a very small camera, etc.), a camera, and/or the like. An RF reader may provide RF energy to the tag, and the tag may use the RF energy to retrieve the identifier from storage and transmit the identifier back to the RF reader. Other electromagnetic and non-electromagnetic methods of or spectrums for wirelessly communicating information will be apparent to those of skill in the art. The range of the wireless reader and/or the tag may be selected to prevent inadvertent reading of the tag by the wireless reader. For example, the tag may need to be within 3, 6, 12, 18, or 24 inches or the like to be read.

Each user (e.g., medical practitioner) that requires access to some or all of the medical monitoring devices at a medical center may receive a tag. The tag may persistently store one or more identifiers and/or an encoded version of the one or more identifiers (e.g., encoded with error correction, encryption, etc.). The wireless reader and/or the medical monitoring device may decode the data received from the tag to determine the one or more identifiers. The identifiers may be unique to each user, unique to each medical monitoring device, and/or some identifiers may be common to multiple users and/or medical monitoring devices. For example, medical practitioners associated with a particular ward may each receive a tag allowing them access to medical monitoring devices in that ward. The tag may include identifiers for medical monitoring devices in that ward, for the particular medical practitioner assigned the tag, for the ward, etc. Tags may include multiple identifiers and/or multiple kinds of identifiers (e.g., a ward identifier, a medical practitioner identifier, and/or one or more medical monitoring device identifiers). The medical monitoring devices may be appropriately configured to authenticate users based on the kind of identifier received, which may include determining which kind of identifier was received. Alternatively, or in addition, a remote device may be responsible for authenticating identifiers and may be appropriately configured. Various divisions of labor between the medical monitoring devices and remote devices, if any, are envisioned (e.g., a medical monitor device may parse and check the format of identifiers read from the tag, and a remote device may authenticate the identifier).

After the user has been authenticated, the user may be able to issue gesture commands to the medical monitoring device. The medical monitoring device may provide an audible and/or visual indication that gesture control has been successfully enabled (e.g., playing a beep, illuminating a light, displaying text, etc.). The medical monitoring device may include a gesture control sensor, which may include one or more cameras. Images from the camera may be analyzed to identify position of one or more limbs of the user. For example, the gesture control sensor may be configured to capture stereoscopic images, and the stereoscopic images may be analyzed to identify the position of the user's limbs. The gesture control sensor and/or a separate processor in the medical monitoring device may be configured to analyze the identified position to determine an action that corresponds to the identified position. For example, the action may include adjusting a setting (e.g., adjusting an alarm setting, adjusting a display setting, etc.), selecting which physiological data or portion of physiological data should be displayed, and/or the like.

Once the user is finished issuing gesture commands, the medical monitor device may disable gesture control. In an embodiment, the user may manually disable gesture control, for example, using a gesture for a disable command and/or by using physical inputs to enter a disable command. Alternatively, or in addition, the medical monitoring device may automatically determine that gesture control should be disabled. The medical monitoring device may disable gesture control a predetermined time after the enabling of gesture control, a predetermined time after a most recent gesture, after a predetermined number of gestures, when the gesture control sensor detects the user leaving a detection area, and/or the like. Users may be able to set the criteria for disabling gesture control.

FIG. 1 is a perspective view of a medical practitioner 150 interacting with a patient 160 coupled to a patient monitor 110 capable of interpreting gestures. The patient monitor 110 may be configured to measure one or more physiological parameters of the patient 160 and display the measurements in a user interpretable format. The medical practitioner 150 may be performing one or more tests on the patient 160 that require the medical practitioner 150 to physically interact with the patient 160. The patient monitor 110 may include a gesture control sensor 115 configured to identify gestures by the medical practitioner 150, determine actions corresponding to the identified gestures, and perform the determined actions. If the gesture control sensor 115 remains enabled, it may accidentally identify the motions by the medical practitioner 150 when interacting with the patient as gestures requiring an action. The patient monitor 110 may perform the action, which may include changing one or more settings, without the knowledge of the medical practitioner 150. The changes resulting from the action may be potentially dangerous for the patient 160.

To prevent the medical practitioner 150 from accidentally entering gesture commands, the gesture control sensor 115 may be disabled. For example, the gesture control sensor 115 may be manually disabled and/or may be automatically disabled, e.g., due to lack of use. Once the gesture control sensor 115 has been disabled, the medical practitioner 150 may be required to re-enable it to enter gesture commands. In the illustrated embodiment, the medical practitioner 150 may be required to provide a tag 120 to re-enable gesture control. The tag 120 may be authenticated to ensure that the medical practitioner 150 is actually permitted to control the patient monitor 110.

For example, each medical practitioner 150 may receive a tag 120 from an owner of the patient monitor 110. In the illustrated embodiment, the tag 120 may be provided on a bracelet 125 so that it can be always worn and easily accessible to the medical practitioner 150. The tag 120 may be an RFID tag attached to a bracelet in the illustrated embodiment but may be a barcode printed on a bracelet, and/or the like in other embodiments. In an embodiment, multiple tags may receive a generic identifier that is common to multiple patient monitors (e.g., all patient monitors in a medical center, all patient monitors in a ward, etc.). Alternatively, or in addition, the tag 120 may include an identifier that is specific to the medical practitioner and/or include one or more identifiers that are each specific to particular patient monitors. Various mappings from identifiers to users, patient monitors, wards, job title, etc. and/or various combinations of mappings are possible in different embodiments and/or configurations. The patient monitor 110 may be configured to determine whether the particular identifiers received permit a user to enter gesture control commands and/or access various features of the patient monitor.

The patient monitor 110 may be configured to read the tag 120 if it is a short distance from the patient monitor 110. Because the tag 120 may be required to be within a short distance, it may be unlikely that the tag 120 will be accidentally read and that gesture control will be enabled when it is not desired. The patient monitor 110 may receive an indication from the medical practitioner 150 that it should read the tag 120 and/or may continuously attempt to read tags. The illustrated wireless tag 120 may be an unpowered, RF tag. The patient monitor 110 may transmit RF energy to the tag 120 to energize the tag 120. The tag 120 may use the received energy to read its identifier and transmit the identifier back to the patient monitor 110. The identifier and/or a transformed version of the identifier (e.g., an encoded or decoded version) may be compared to local and/or remote storage to determine whether to enable gesture control. Gesture control may remain enabled until criteria for disabling it are met.

Figure 2:
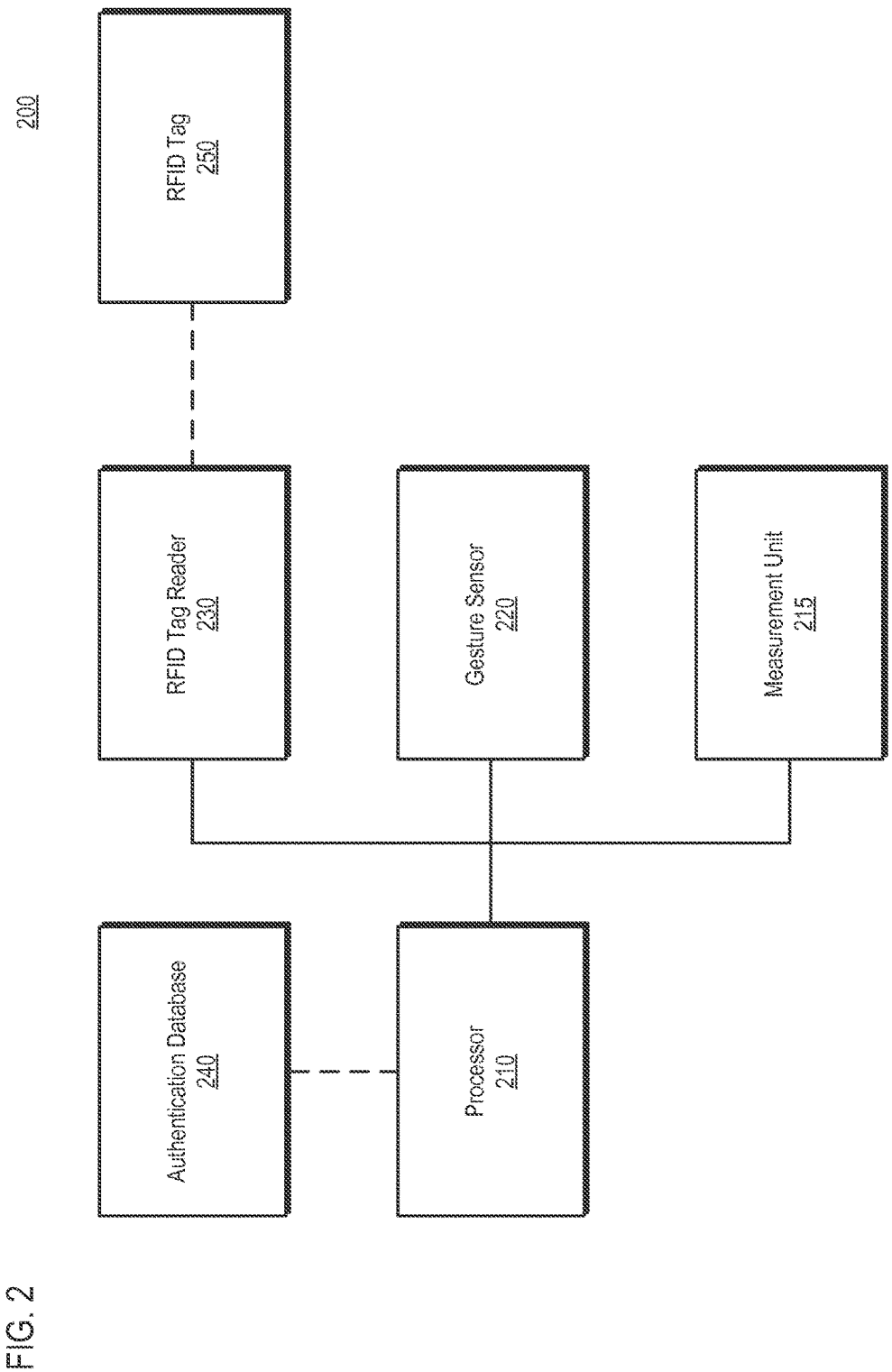
FIG. 2 is a block diagram of a system for authenticating an RFID tag.

FIG. 2 is a block diagram of a system 200 for authenticating an RFID tag 250. The system 200 may include a processor 210. The processor 210 may be communicatively coupled to and/or control a plurality of sensors and/or interfaces 215, 220, 230 and may operate on data received from the plurality of sensors and/or interfaces 215, 220, 230. For example, a measurement unit 215 may be configured to measure one or more physiological parameters of a patient. The processor 210 may convert the received physiological data into a format that can be displayed to users (e.g., a waveform, a numerical value, etc.).

A gesture sensor 220 may be configured to identify gestures provided by users. The gesture sensor 220 may provide an indication and/or representation of identified gestures to the processor 210 and/or may provide raw data from which the processor 210 can identify gestures. The processor 210 may determine what action corresponds to the indicated gesture and may perform the determined action. The processor 210 may also, or instead, determine when the gesture sensor 220 should be disabled. The processor 210 may disable the gesture sensor 220 by shutting it down to a mode where little or no power is consumed by the gesture sensor 220. Alternatively, or in addition, the processor 210 may ignore gestures that are received from the gesture sensor 220 but allow the gesture sensor 220 to continue to identify gestures when gesture control is disabled.

A wireless reader 230 may be configured to read an identifier from the RFID tag 250. For example, the wireless reader 230 may energize the RFID tag 250 and may receive the identifier from the RFID tag 250 in response. The wireless reader 230 may provide any initial decoding and/or parsing of the response and/or identifier before providing the identifier to the processor 210. The processor 210 may authenticate the identifier to determine whether the gesture sensor 220 should be enabled (e.g., if it is currently disabled).

The processor 210 may compare the identifier to one or more entries in an authentication database 240 to determine what gesture control rights are associated with the identifier. The authentication database 240 may be stored locally and/or may be remotely accessible (e.g., via a computer network). For a remotely accessible authentication database 240, the processor 210 may instruct a wireless communication interface (not shown) to request that the authentication database 240 authenticate an identifier. The authentication database 240 may determine whether the identifier matches an existing entry in the authentication database 240 and/or the rights associated with the identifier. Various divisions of labor between the processor 210 and the authentication database 240 are contemplated. For example, the authentication database 240 may determine which database entries should be returned to processor 210 and/or may return all information associated with an entry for analysis by the processor 210. The processor 210 may control the gesture sensor 220 based on the information received from the authentication database.

Figure 3:
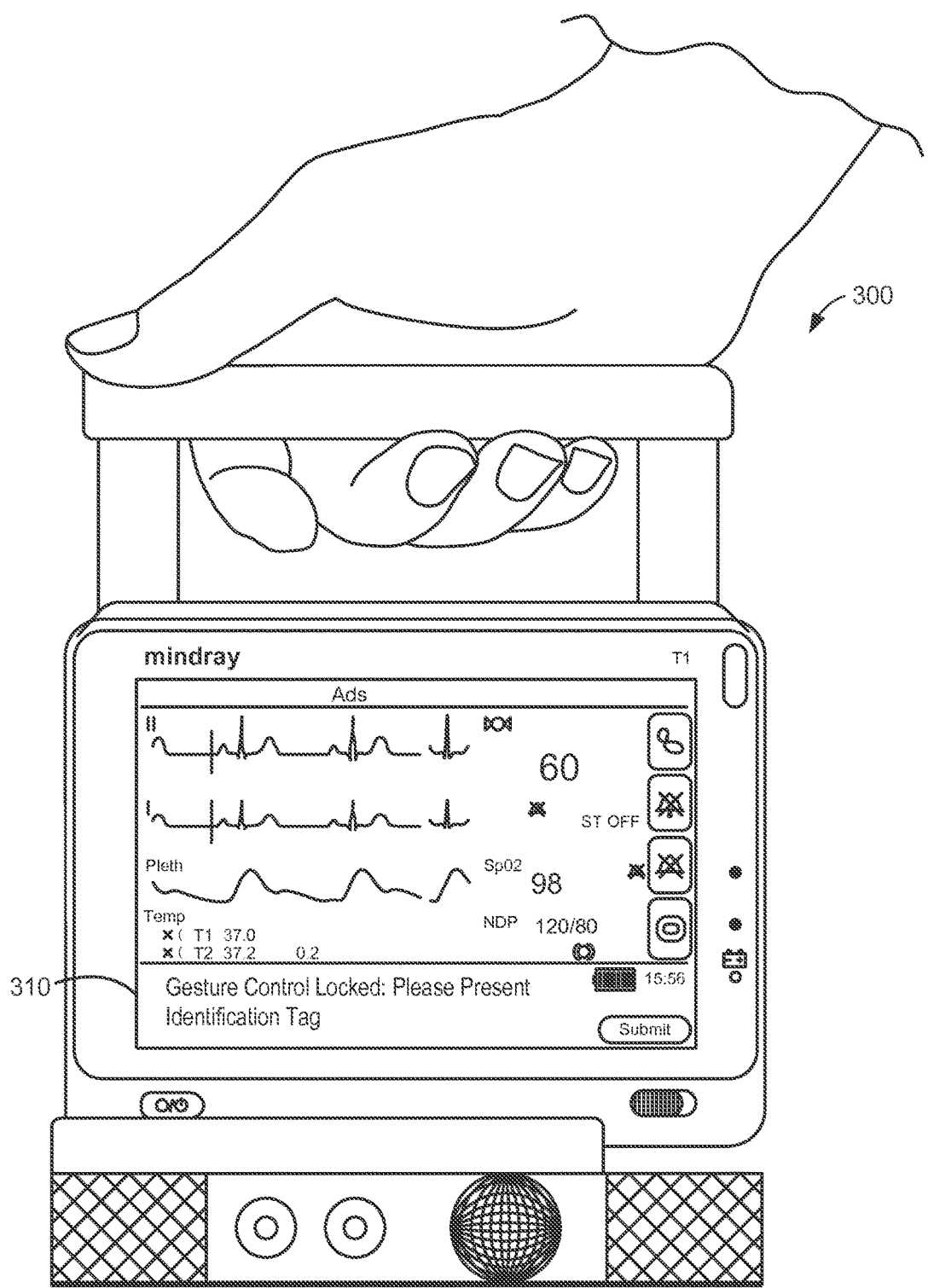
FIG. 3 is a perspective view of a patient monitor presenting an exemplary screen display indicating a state of a gesture control sensor.

FIG. 3 is a perspective view of a patient monitor 300 presenting an exemplary screen display indicating a state of a gesture control sensor. In the illustrated state, the patient monitor 300 is presenting a message 310 indicating that gesture control is currently locked and that a tag will need to be presented in order for gesture control to be unlocked. The message 310 may be displayed as long as gesture control is locked and/or may be presented temporarily in response to user attempts to provide a gesture (e.g., the gesture control sensor may remain powered while it is disabled). In some embodiments, the user may be able to remove the message if the user is no longer interested in seeing it. For example, the user may be able to close the message 310, and/or the user may be able to adjust the settings that determine whether or not a message is displayed.

Figure 4:
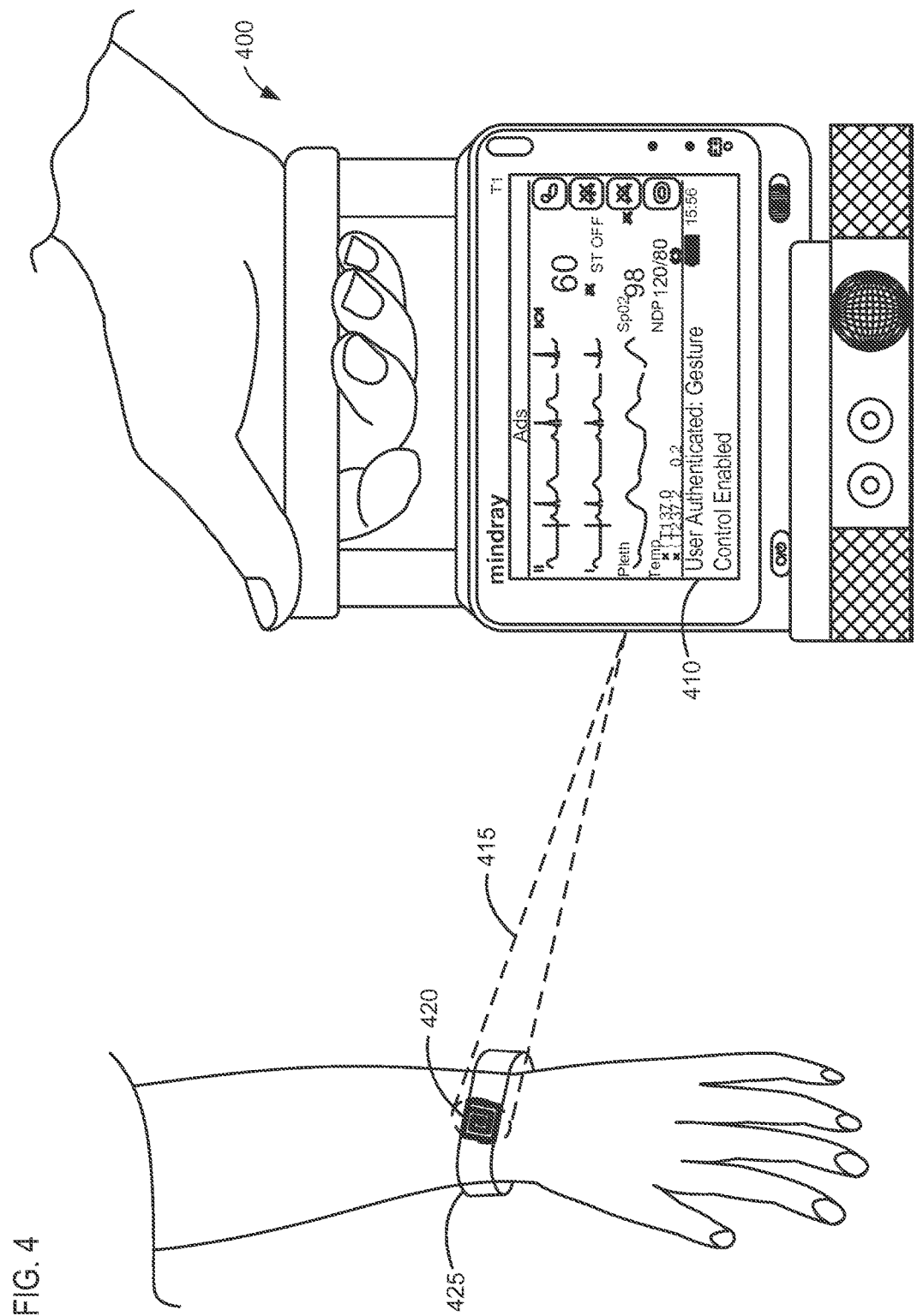
FIG. 4 is a perspective view of a patient monitor in the process of reading a wireless tag.

FIG. 4 is a perspective view of a patient monitor 400 in the process of reading a wireless tag 420. A user may have moved a bracelet 425 including the tag 420 near the patient monitor 400 such that the tag 420 is close enough to be read by the patient monitor 400. The patient monitor 400 may have been continuously scanning for nearby tags and/or may have received a user indication that it should scan for the tag 420. The patient monitor 400 may scan for the tag 420 by emitting RF energy 415 that can be used to power the tag 420. The tag 420 may use the received energy to look up an identifier and transmit it back to the patient monitor 400. In other embodiments, the tag 420 may be a barcode rather than an RFID tag, and the RF energy 415 may instead be a laser for reading the barcode rather than RF energy 415.

The patient monitor 400 may also display a message 410 indicating a current status of the attempt to read the tag 420. In the illustrated state, the identifier from the tag 420 has just been authenticated, so the message 410 includes an indication that the user has been authenticated successfully and that gesture control has been enabled. In other states and/or embodiments, the message 410 may indicate that the patient monitor 400 is scanning for tags 420, reading the tag 420, authenticating an identifier from the tag 420, and/or the like. The message 410 may be displayed for a short time before being hidden, but gesture control may remain enabled for a longer period of time. Alternatively, the patient monitor 400 may not display a message 410 in some embodiments and may instead display an indicator, such as a light, a symbol, text, etc. indicating that gesture control has been enabled.

Figure 5:
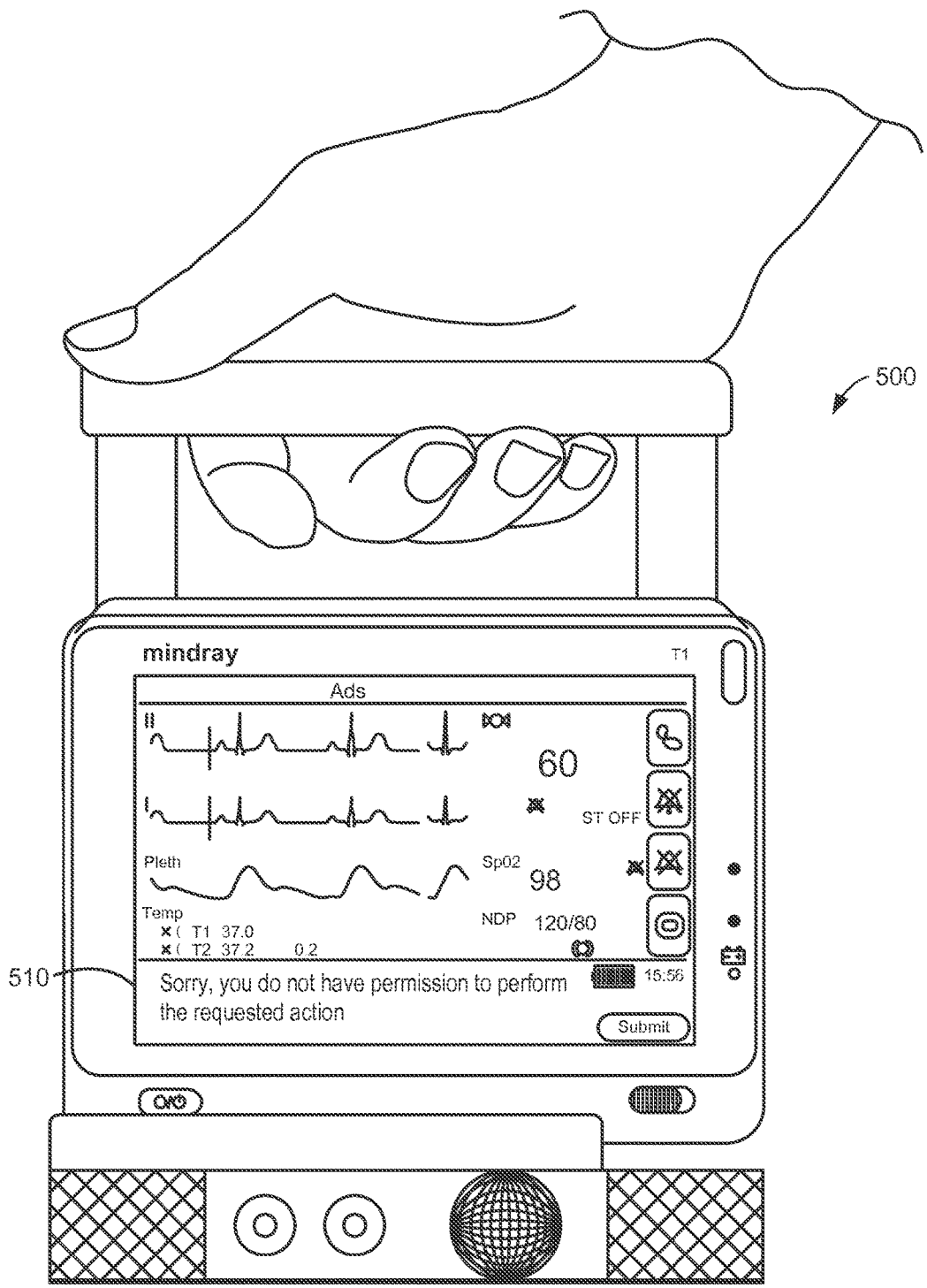
FIG. 5 is a perspective view of a patient monitor presenting an exemplary screen display indicating the user's control rights.

FIG. 5 is a perspective view of a patient monitor 500 presenting an exemplary screen display indicating the user's control rights. Once gesture control has been enabled, the user may attempt to enter commands. The user may only have partial access rights and may be able to enter some commands but not others. In the illustrated embodiment, the user may have attempted to enter a command that the user did not have the rights to enter. For example, a ward of a medical center may have a predetermined set of configurations that must be applied on all patient monitors. Only a director of the ward may be able to change that set of configurations, so commands from other users that attempt to change them may be refused. The patient monitor 500 may display a message 510 to the user indicating that the command has been refused and/or the reason for refusal. In the illustrated case, the message 510 may indicate that the user does not have permission to enter the command received by the patient monitor. Alternatively, or in addition, the message 510 may indicate when a gesture was not recognized, when the patient monitor 500 is not physically able to execute the command, and/or the like. The message 510 may be hidden after a predetermined time period has expired.

Figure 6:
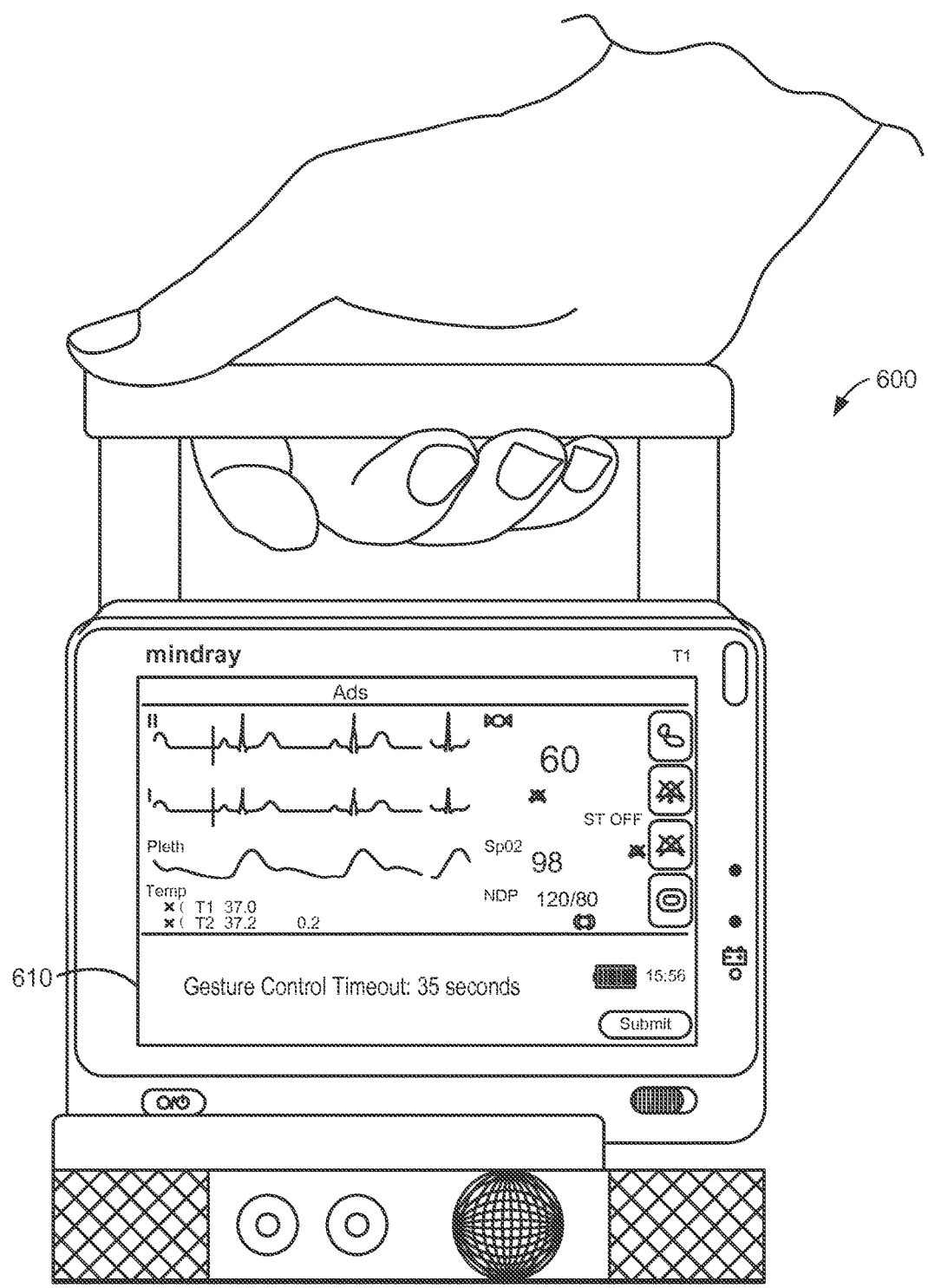
FIG. 6 is a perspective view of a patient monitor presenting an exemplary screen display indicating a current state of the patient monitor relative to criteria for disabling gesture control.

FIG. 6 is a perspective view of a patient monitor 600 presenting an exemplary screen display indicating a current state of the patient monitor 600 relative to criteria for disabling gesture control. The patient monitor 600 may give users advanced warning before disabling gesture control. The user may be able to gesture a stay alive command and/or otherwise prevent the criteria from being satisfied if the user so desires. In the illustrated configuration, the patient monitor 600 is configured to disable gesture control a predetermined time after a particular event (e.g., a last gesture command, a last reading of an identifier from a tag, etc.). The patient monitor 600 may display a message 610 indicating the time left until the criteria is satisfied and gesture control is disabled. The message 610 may countdown the time and/or display messages at different time increments. Different messages may be displayed depending on which criteria are going to cause the gesture control to be disabled. For example, the message 610 may indicate that a disable gesture control command has been received and that another should be entered to confirm the command in an embodiment. When the criteria is satisfied, the patient monitor 600 may indicate that gesture control is being disabled and/or may simply indicate that gesture control has been disabled and that the user will have to present an identification tag to re-enable gesture control.

Figure 7:
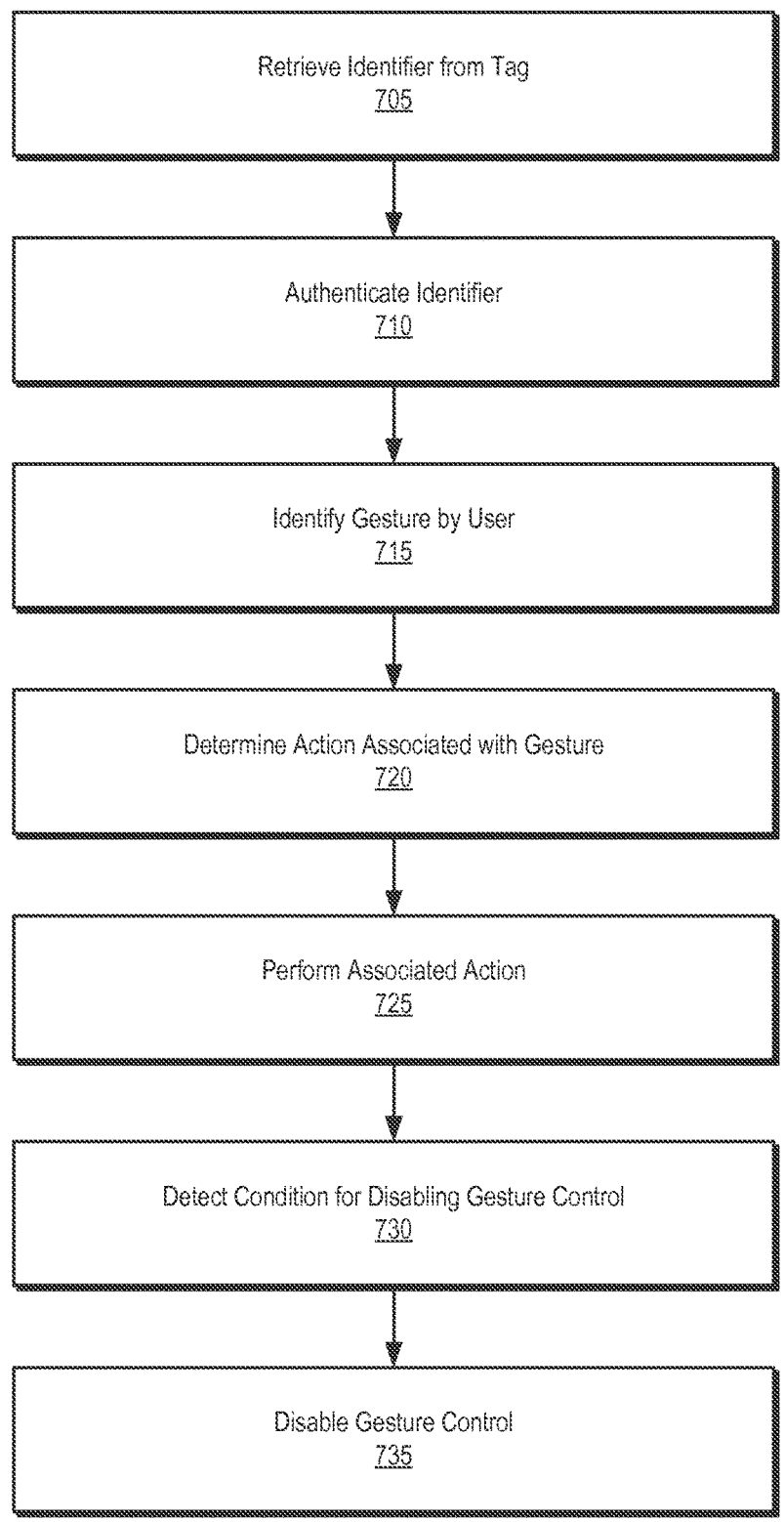
FIG. 7 is a flow diagram of an embodiment of a method for controlling access to a medical monitoring device.

FIG. 7 is a flow diagram of an embodiment of a method 700 for controlling access to a medical monitoring device. The method 700 may begin by retrieving 705 an identifier from a tag. For example, the medical monitoring device may have previously disabled gesture control and/or started in a state with gesture control disabled. Retrieving 705 may be attempted in response to a user indication to do so, periodically, continuously, and/or the like. The identifier may be retrieved 705 from an RF tag (e.g., using an RF reader, etc.), from a barcode (e.g., using a laser, a small camera, etc.), and/or the like. Retrieving 705 may include transmitting energy (e.g., RF energy, light, etc.) to the tag so that the tag can return the identifier. Retrieving 705 may include any decoding, error checking/correcting, decrypting, and/or parsing of the received data that is necessary to extract the identifier.

The identifier may be authenticated 710 to determine whether to enable gesture control. Authenticating 710 may include determining whether the identifier has the right to enable gesture control and/or which gesture commands are permitted for that identifier. Authenticating 710 may include comparing the identifier to one or more stored values. The values may be stored locally and/or on remote storage that is accessible. The remote and/or local storage may include explicit indications of the rights associated with the identifier, and/or the identifier may be associated with characteristics that can be used to determine the rights (e.g., job title, position within an organizational hierarchy, ward, etc.). Gesture control for some and/or all commands may be enabled based on the authenticating 710.

A gesture by the user may be identified 715. A gesture sensor including one or more cameras may be used to identify the gesture by the user. The gesture sensor may determine the position of limbs, hands, and/or fingers of the user. Alternatively, or in addition, the gesture sensor may output video data that includes depth information, and a processor may determine the position of the limbs, hands, and/or fingers. A representation of the relative arrangement of limbs, hands, and/or fingers may be compared to one or more stored values to determine if a match is found. If a match is found, the matching gesture may be identified as the gesture. Otherwise, it may be assumed that the user is not gesturing. False positives may be guarded against, for example, by requiring the gesture be held a certain length of time and/or that the gesture include a particular movement.

An action may be determined 720 based on the gesture identified 715. For example, a mapping from gestures to executable actions may be stored locally and/or remotely to convert the gestures. The actions may include accessing menus, settings, etc.; zooming, rewinding, mathematically manipulating, etc. displayed data; enabling or disabling measurement sensors; and/or the like. Once the action has been determined 720, it may be performed 725. The action may be treated like any other input that can be handled by an appropriate module of software operating on the medical monitoring device. A processor may execute the instructions necessary to achieve the desired outcome. The user may be able to provide additional gestures, so identifying 715 gestures, determining 720 actions, and performing 725 the actions may be repeated for additional gestures provided by the user.

Eventually, conditions for disabling gesture control may be detected 730. Predetermined criteria for disabling gesture control may be evaluated periodically and/or in response to user input. For example, the predetermined criteria may include a time since a last gesture, a time since last reading a tag, a number of gestures entered, a location of the user, a gesture command received, a physical input from the user, and/or the like. If the predetermine criteria is satisfied, gesture control may be disabled 735. Once gesture control has been disabled 735, the method 700 may return to an idle state and may wait until a tag is proximate enough for an identifier to be retrieved 705 from the tag.

Embodiments may include various steps, which may be embodied in machine-executable instructions to be executed by a computer system. A computer system includes one or more general-purpose or special-purpose computers (or other electronic devices). The computer system may include hardware components that include specific logic for performing the steps or may include a combination of hardware, software, and/or firmware.

Embodiments may also be provided as a computer program product including a computer-readable medium having stored thereon instructions that may be used to program a computer system or other electronic device to perform the processes described herein. The computer-readable medium may include, but is not limited to: hard drives, floppy diskettes, optical disks, CD ROMs, DVD ROMs, ROMs, RAMs, EPROMs, EEPROMs, magnetic or optical cards, solid-state memory devices, or other types of media/computer-readable media suitable for storing electronic instructions.

Computer systems and the computers in a computer system may be connected via a network. Suitable networks for configuration and/or use as described herein include one or more local area networks, wide area networks, metropolitan area networks, and/or "Internet" or IP networks, such as the World Wide Web, a private Internet, a secure Internet, a value-added network, a virtual private network, an extranet, an intranet, or even standalone machines which communicate with other machines by physical transport of media (a so-called "sneakernet"). In particular, a suitable network may be formed from parts or entireties of two or more other networks, including networks using disparate hardware and network communication technologies.

One suitable network includes a server and several clients; other suitable networks may contain other combinations of servers, clients, and/or peer-to-peer nodes, and a given computer system may function both as a client and as a server. Each network includes at least two computers or computer systems, such as the server and/or clients. A computer system may include a workstation, laptop computer, disconnectable mobile computer, server, mainframe, cluster, so-called "network computer" or "thin client," tablet, smart phone, personal digital assistant or other hand-held computing device, "smart" consumer electronics device or appliance, medical device, or a combination thereof.

The network may include communications or networking software, such as the software available from Novell, Microsoft, Artisoft, and other vendors, and may operate using TCP/IP, SPX, IPX, and other protocols over twisted pair, coaxial, or optical fiber cables, telephone lines, radio waves, satellites, microwave relays, modulated AC power lines, physical media transfer, and/or other data transmission "wires" or wireless protocols known to those of skill in the art. The network may encompass smaller networks and/or be connectable to other networks through a gateway or similar mechanism.

Each computer system includes at least a processor and a memory; computer systems may also include various input devices and/or output devices. The processor may include a general purpose device, such as an Intel®, AMD®, or other "off-the-shelf" microprocessor. The processor may include a special purpose processing device, such as an ASIC, SoC, SiP, FPGA, PAL, PLA, FPLA, PLD, or other customized or programmable device. The memory may include static RAM, dynamic RAM, flash memory, one or more flip-flops, ROM, CD-ROM, disk, tape, magnetic, optical, or other computer storage medium. The input device(s) may include a keyboard, mouse, touch screen, light pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computer systems may be capable of using a floppy drive, tape drive, optical drive, magneto-optical drive, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and predefined manner as described herein.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer executable code located within a memory device. A software module may, for instance, include one or more physical or logical blocks of computer instructions, which may be organized as a routine, program, object, component, data structure, etc., that perform one or more tasks or implement particular abstract data types.

In certain embodiments, a particular software module may include disparate instructions stored in different locations of a memory device, different memory devices, or different computers, which together implement the described functionality of the module. Indeed, a module may include a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that can be used according to the present invention is already available, such as: general purpose computers; computer programming tools and techniques; computer networks and networking technologies; digital storage media; authentication; access control; and other security tools and techniques provided by public keys, encryption, firewalls, and/or other means.

It will be understood by those having skill in the art that many changes may be made to the details of the above-described embodiments without departing from the underlying principles of the disclosure. The scope of the present disclosure should, therefore, be determined only by the following claims.

The invention claimed is:

1. A medical monitoring device comprising:
a measurement component configured to receive, from at least one sensor,
physiological data representative of a physiological condition of a patient; a gesture sensor configured to determine a gesture by a user; a wireless reader configured to read a tag presented by the user and retrieve an identifier from the tag; a processing unit configured to:
enable gesture control in response to the wireless reader retrieving the identifier,
generate an indication of a status of the gesture control when a gesture is not recognized or when the medical monitoring device is unable to execute the command,
generate an indication of a current status of the wireless reader of an attempt to read the tag presented by the user, the current status including scanning for the tag, reading the tag, or authenticating the identifier from the tag, determine an action to perform in response to the gesture; and a display configured to display the indication of the status of the gesture control and the indication of the current status of the wireless reader.

2. The medical monitoring device of claim 1, wherein the processing unit is configured to disable the gesture sensor when gesture control is disabled.

3. The medical monitoring device of claim 1, wherein the processing unit is configured to disable gesture control a predetermined time after retrieving the identifier.

4. The medical monitoring device of claim 1, wherein the processing unit is configured to disable gesture control a predetermined time after a most recent gesture.

5. The medical monitoring device of claim 1, wherein the processing unit is configured to authenticate the identifier from the tag before enabling gesture control.

6. The medical monitoring device of claim 5, wherein the processing unit is configured to communicate with a medical center network to authenticate the identifier.

7. The medical monitoring device of claim 1, wherein the range of the wireless reader is selected to prevent inadvertent interaction with the tag.

8. The medical monitoring device of claim 1, wherein the tag is selected from the group consisting of a radio frequency identification tag and a barcode.

9. A method for controlling access to a medical monitoring device, the method comprising:
the medical monitoring device reading a tag presented by a user and retrieving an identifier from the tag presented by a user;
the medical monitoring device enabling gesture control in response to retrieving the identifier;
the medical monitoring device generating an indication of a status of the gesture control when a gesture is not recognized or when the medical monitoring device is unable to execute the command;
the medical monitoring device generating an indication of a current status of the wireless reader of an attempt to read the tag presented by the user, the current status including scanning for the tag, reading the tag, or authenticating the identifier from the tag;
the medical monitoring device displaying the indication of the gesture control and the indication of the current status of the wireless reader;
the medical monitoring device determining a gesture by the user; and
the medical monitoring device determining an action to perform in response to the gesture.

10. The method of claim 9, further comprising disabling gesture control a predetermined time after retrieving the identifier.

11. The method of claim 9, further comprising disabling gesture control a predetermined time after a most recent gesture.

12. The method of claim 9, further comprising authenticating the identifier from the tag before enabling gesture control.

13. The method of claim 12, wherein authenticating the identifier comprises communicating with a remote device to authenticate the identifier.

14. The method of claim 9, wherein retrieving the identifier comprises retrieving the identifier when the tag is within a predetermined distance of the medical monitoring device.

15. The method of claim 9, wherein the tag is selected from the group consisting of a radio frequency identification tag and a barcode.

16. A medical monitoring device comprising a non-transitory computer readable medium further comprising program code, which, when executed by a processor, causes the processor to:
cause a wireless reader to retrieve an identifier from a tag;
enable gesture control in response to the wireless reader retrieving the identifier; generate an indication of a status of the gesture control when a gesture is not recognized or when the medical monitoring device is unable to execute the command,
generate an indication of a current status of the wireless reader of an attempt to read the tag presented by the user, the current status including scanning for the tag, reading the tag, or authenticating the identifier from the tag, display the indication of the status of the gesture control and the indication of the current status of the wireless reader;
determine a gesture by the user; and
determine an action to perform in response to the gesture.

17. The medical monitoring device of claim 16, wherein the program code causes the processor to disable gesture control a predetermined time after a most recent gesture.

18. The medical monitoring device of claim 16, wherein the program code causes the processor to authenticate the identifier from the tag before enabling gesture control.

19. The medical monitoring device of claim 18, wherein the processor authenticates the identifier by communicating with a medical center network.

20. The medical monitoring device of claim 16, wherein the tag is selected from the group consisting of a radio frequency identification tag and a barcode.

* * * * *